United States Patent [19]
Nadoolman et al.

[11] Patent Number: 5,788,982
[45] Date of Patent: Aug. 4, 1998

[54] METHOD AND COMPOSITION FOR TREATING ORAL PAIN USING CAPSAICIN

[76] Inventors: Wolffe Nadoolman, 111 Park St., Apt. 15T; Linda M. Bartoshuk, 495 Ellsworth Ave., both of New Haven, Conn. 06511

[21] Appl. No.: 491,083
[22] Filed: Jun. 16, 1995
[51] Int. Cl.$^6$ ............................................. A61K 9/68
[52] U.S. Cl. ........................................ 424/440; 424/39
[58] Field of Search ............................... 424/440, 439

[56] References Cited

U.S. PATENT DOCUMENTS

| | | | |
|---|---|---|---|
| 5,079,260 | 1/1992 | Weitzberg | 514/532 |
| 5,288,497 | 2/1994 | Stanley | 424/440 |
| 5,496,828 | 3/1996 | Cullinan | 514/324 |

*Primary Examiner*—Thurman K. Page
*Assistant Examiner*—D. Faulkner
*Attorney, Agent, or Firm*—Burns, Doane, Swecker Mathis, LLP

[57] ABSTRACT

A vehicle useful for delivery of capsaicin that is convenient, and acceptable to patients, and which insures sufficient exposure to the capsaicin to produce desensitization is the subject of this invention. The applicants have developed a candy vehicle for the delivery of capsaicin. Candies containing 5–9 ppm capsaicin were made by adding cayenne pepper to a standard candy carrier recipes.

1 Claim, No Drawings

METHOD AND COMPOSITION FOR TREATING ORAL PAIN USING CAPSAICIN

BACKGROUND OF THE INVENTION

Oral mucositis is a significant problem in patients receiving chemotherapy or radiation therapy. Estimates of oral mucositis in cancer therapy range from 40% receiving standard chemotherapy to 76% in bone marrow transplant patients. Virtually all patients who receive radiation therapy to the head and neck develop oral complications. Mucositis is not only painful, but can limit adequate nutritional intake, and can decrease willingness of patients to continue treatment. More severe mucositis with extensive ulceration may require costly hospitalizations with parenteral nutritional support and narcotics. Mucositis not only diminishes the quality of life, it may result in serious clinical complications. Healthy oral mucosa serves to clear microorganisms and provides a chemical barrier that limits penetration of many compounds into the epithelium. A mucosal surface that is damaged increases risk of a secondary infection and may even prove to be a nidus for systemic infection. Mucositis may result in the need to reduce dosage in subsequent chemotherapy cycles or to delay radiation therapy, which may ultimately affect patient response to therapy.

DIRECT STIMATOTOXICITY

Normally, cells of the mouth undergo rapid renewal over a 7 to 14 day cycle. Both chemotherapy and radiation therapy interfere cellular mitosis and reduce the ability of the oral mucosa to regenerate. Cancer chemotherapeutic drugs that produce direct stomatotoxicity include the alkylating agents, antimetabolites, natural products, and other synthetic agents such as hydroxyurea and procarbazine hydrochloride (2). Typical sequelae of these cytotoxic agents include epithelial hyperplasia, collagen and glandular degeneration, and epithelial dysplasia (3). Mucositis is an inevitable side-effect of radiation. The severity of the mucositis is dependent on the type of ionizing radiation, the volume of irradiated tissue, the dose per day, and the cumulative dose. As the mucositis becomes more severe, pseudomembranes and ulcerations develop. Poor nutritional status further interefers with mucosal regeneration by decreasing cellular migration and renewal (2).

Direct stomatotoxicity is usually seen 5 to 7 days after the administration of chemotherapy or radiation therapy. In the nonmyelosuppressed patient oral lesions heal within 2 to 3 weeks. The mucosa that is most affected is the nonkeratinized mucosa. The most common sites include the labial, buccal, and soft palate mucosa, as well as the floor of the mouth, and the ventral surface of the tongue. The inflammatory-like changes may begin as a white discoloration or as an erythema of the mucosa.

A mucositis grading system gives the physician the ability to assess the severity of the mucositis both in terms of the pain and the ability of the patient to maintain adequate nutrition so that a treatment plan can be appropriately constructed. There are many different grading systems; however, most of them are based on two or more clinical parameters including erythema, pain, and problems with eating. An example of a common grading system is that proposed by the National Cancer Institute which uses a numbering scale of 0 to 4. Grade 0 means no mucositis; grade 1, the patient has painless ulcers, erythema, or mild soreness; grade 2, the patient has painful erythema, edema, or ulcers but can eat; grade 3, the patient has painful erythema, edema or ulcers, and cannot eat; and grade 4, the patient requires parenteral or enteral support. At the 1989 National Institute of Health consensus conference on oral complications of cancer therapy, clinicians and researchers agreed that effective prevention of mucositis requires a comprehensive patient examination to identify potentially complicating oral disease before the cancer therapy begins. Significant problems that must be corrected include poor oral hygiene, periapical pathology, third molar pathology, periodontal disease, dental caries, defective restorations, orthodontic appliances, ill-fitting prostheses, and any other potential source of infection. Bacterial and fungal surveillance cultures are not necessary, however prophylactic use of acyclovir should be considered in patients who are seropositive and at high risk for reactivating Herpes Simplex Virus infection, such as those who undergo bone marrow transplant or have prolonged and pronounced myelosuppression. If a diagnosis is made of a fungal, viral, or bacterial infection along with the mucosal lesions, prompt treatment is necessary to avoid the risk of systemic infection.

TRADITIONAL REMEDIES FOR THE PREVENTION AND TREATMENT OF MUCOSITIS

A standardized approach for the prevention and treatment of chemotherapy and radiation induced mucositis is essential, though unfortunately the efficacy and safety of most of the regimens used have not been established. The prophylactic measures that are usually employed for the prevention of mucositis include chlorhexidine gluconate (Peridex), saline rinses, sodium bicarbonate rinses, acyclovir, amphotericin and/or ice. Regimens commonly utilized for the treatment of mucositis and the pain associated with the mucositis include a local anesthetic such as lidocaine or dyclone, Maalox or Mylanta, diphenhydramine (Benedryl), nystatin, or sucralfate. These agents are either used alone, or in different combinations consisting of several of the above medications made into a mouthwash. Other agents used less commonly used include Kaopectate, allopurinal, Vitamin E, beta-carotene, aspirin, antiprostaglandins, prostaglandins, MGI 209marketed as oratect gel, silver nitrate and antibiotics. Oral and sometimes parenteral narcotics are utilized to relieve the pain caused by the mucositis.

Sucralfate, a successful treatment for gastric ulceration, has been tested as a rinse for the treatment of mucositis. Data from these studies are conflicting. Anecdotal experience suggests sucralfate might be useful in the treatment of chemotherapy induced mucositis. A doubleblind placebo-controlled cross-over study done with forty patients receiving cis-platin and continuous infusion with 5-fluorouracil found a reduction in edema, erythema, erosion and ulcerations, with a patient preference which favored sucralfate, but this did not reach statistical significance. In contrast, results from a similarly designed study with patients receiving remission-induction chemotherapy for acute non-lymphocytic leukemia did not support the amelioration of stomatitis. The latter study also concluded that the chronic administration of the sucralfate suspension had no effect on the incidence of gastrointestinal bleeding and ulceration. The authors did note that some patients reported pain relief from sucralfate (7). Preliminary data from a Phase III randomized trial completed by the Illinois Cancer Council suggests that a topical solution of sucralfate is superior to a solution of Benadryl, Maalox and Xylocaine. Both treatments provided equal pain relief and equal use of supplemental analgesics; however, five days after treatment initiation, a greater percentage of patients in the sucralfate group had less severe mucositis than the group receiving the Benadryl, Maalox, and Xylocaine combination. Vitamins in pharmacologic doses have also been used to treat mucositis. Clinicians use Vitamin E for chemotherapy-induced mucositis because it can stabilize cellular membranes, and may improve herpetic gingivitis, possibly through antioxidant activity (8–10). The efficacy of Vitamin E to improve chemotherapy induced mucositis was demonstrated in a placebo-controlled trial (11, 12). Since both sucralfate and Vitamin E provide some effectiveness in mucositis, the Eastern Cooperative Oncology Group is in the process of a Phase III study of sucralfate versus Vitamin E for treatment induced mucositis. Beta-Carotene, a Vitamin A derivative with antioxidant properties, has also been evaluated in a pilot study. It was found that beta-carotene may be beneficial in reducing mucositis induced by both chemotherapy and radiation therapy (13). Allopurinal is another agent that has been evaluated for the prevention and treatment of oral mucositis induced by 5-FU chemotherapy. The rationale for the allopurinal mouthwash was based on data that systemic allopurinal was able to decrease 5- induced toxicity by inhibiting the enzyme orotidylate decarboxylase and the formation of the metabolites of fluorodeoxyuridine monophosphate (FdUMP) and fluorouridine (FUTP) (14). Two pilot studies support the use of allopurinol for oral mucositis. One by Clark and Slevin revealed that allopurinal mouthwash substantially decreased the incidence and severity of mucositis in six patients who received bolus 5-FU chemotherapy ( 15). Another pilot study done in 16 patients receiving 5-day intravenous 5FU infusions, utilizing allopurinal mouthwashes four to six times per day, also found that the allopurina'l alleviated the mucositis in all of the patients ( 16). After the success in the pilot studies, the use of allopurinal became routine medical practice in many institutions. The efficacy of allopurinal was tested by the North Central Cancer Treatment Group and the Mayo Clinic in a randomized, double-blind clinical trial. Seventy-five patients were assigned to receive an allopurinal mouthwash or a placebo while they received their first 5-day course of 5-FU with or without leucovorin. This study demonstrated no protective effect against 5-FU induced mucositis by the allopurinal regimen ( 17). After finding that allopurinal mouthwash was not protective against 5-FU induced mucositis, the North Central Cancer Treatment Group and the Mayo Clinic undertook a controlled trial of oral cryotherapy for preventing stomatitis in patients receiving 5-FU (18, 19). The study found that cryotherapy is helpful in reducing the severity of 5-FU induced mucositis. Additional well controlled trials are needed to confirm that cryotherapy is useful in reducing the severity of mucositis.

Many different topical preparations are used for the management of treatment-induced mucositis with the idea that maintaining oral hygiene and reducing inflammation will decrease the severity of the mucositis. Those include chlorhexidine gluconate, sodium bicarbonate, povidoneiodine, saline, gentian violet, and aspirin. Epstein and Stevenson-Moore found, in a double-blind placebo controlled trial, that benzydamine, a topical nonsteroidal antiinflammatory agent only available in Europe and Canada, produced statistically significant relief of pain from treatmentinduced mucositis (20). Positive responses to benzydamine were reported in at least two other studies (21, 22). However, a study done comparing chlorhexidine and benzyamine mouthwashes found no significant differences in mucositis scores, overall pain scores, or the yeast and bacterial species with either treatment (23). In addition, a randomized trial of chlorhexidine mouthwash suggested that it not only failed to benefit patients with mucositis, the patients actually experienced discomfort from the mouthwash (24).

Both prostaglandins (PGE2) and antiprostaglandins have been studied in the prevention and treatment of mucositis. The topical administration of PGE2 was found to decrease pain secondary to mucositis (25, 26). However, paradoxically, a study demonstrated that indomethacin, an antiprostaglandin, given orally reduced the severity and delayed the onset of mucositis induced by radiation therapy (27). Other topical agents that have been examined include MGI 209, marketed as oratect gel (28, 29), silver nitrate in radiation induced mucositis (30), and Kamillosan liquid (31).

Another approach that has been utilized includes the administration of lozenges with antibiotics that selectively eliminate gram-negative bacilli. Spijkervet et. al. found a reduced frequency of severe mucositis with the administration of lozenges made of polymyxin E tobramycin, and amphotericin (32, 33). Preliminary data suggest that patients who received human recombinant granulocyte colony-stimulating factor with chemotherapy for transitional cell carcinoma of the bladder also had a reduction in mucositis (33). Several anesthetic cocktails, with agents such as viscous xylocaine or dyclonine hydrochloride have been used with some success (34). The anesthetic agents relieve the patient's pain, however this relief is temporary and also prevents taste perception which can further interfere with food intake. Other analgesics and mucosal coating agents that can control pain include Kaopectate, Benadryl, Orabase, and Oratect Gel. Even though clinicians use these agents, there is no experimental evidence to establish the efficiency of any of them (35). Many of the agents discussed above may have some value in palliating pain; however, there are very few controlled clinical trials which establish their efficacy. At the present time there is no standard treatment for the prevention or treatment of mucositis. When the mucositis is severe and interferes with nutritional intake and quality of life, it is appropriate to use any of the treatments that have been mentioned above, as well as oral or if necessary parenteral narcotics. In order to discover an efficacious treatment it is essential to continue studies of the treatments already available and to develop any promising new approaches.

PLANTS, HERBS, AND OTHER POTIONS FOR PAIN AND RELIEF

Through the years ancient cultures learned by trial and error that many natural substances could be used to decrease the sensation of pain or even produce a loss of consciousness. In the seventeenth and eighteenth century, plants such as peppermint and camphor were used for the pain of skin lesions, cool moist clay was used to relieve sunburn pain, and witchhazel oil was found to relieve dermal and muscular aches and pains. Traditional chemical remedies used centuries ago such as alcohol, opium, and coca, remain part of our armamentarium today for the control of pain (36). Capsaicin, the active ingredient in chili peppers, is one such remedy that has been used through the years, and may prove beneficial for mucositis pain induced by chemotherapy and radiation therapy. The remainder of this review provides background and initial support for use of capsaicin for control of oral mucositis pain.

FIELD OF THE INVENTION

The present invention realtes to the use of capsaicin compositions to treat oral pain. Capsaicin is a topical agent that has been used recently for the treatment of such problems as post-herpetic neuralgia and arthritis but which also has an ancient history as a remedy for oral pain. However, particular uses of capsaicin to treat oral pain ahve been limited in the scope of their effectiveness and ease of use.

DETAILED DESCRIPTION OF THE INVENTION

History of Chili Peppers

Botanical origins. Columbus is credited with introducing chili peppers to Europe (37). One of the motivations for his explorations was to find a new route to the Orient, the source of black pepper. The similarity of the oral irritation of black pepper and the chili peppers of the new world led to the name "pepper" for the chilis although they are not botanically related to the black pepper. Chili peppers are botanically related to the tomato, potato, tobacco, and nightshade. The consumption of chili peppers dates back to 7000 B.C. in Mesoamerica (38). It's medicinal use is documented in a variety of sources (37). Particularly interesting in the present context, Sahagun, a Franciscan monk living in Mexico in the 16th century attributed this remedy to the Aztecs (39): "An injury to the tongue; biting of the tongue; laceration of the tongue. Its treatment is to cook chili (with) salt, which is to be spread on. Then bee honey or thickened maguey syrup is to be spread on." Suzuki and Iwai provide a history of the early chemical studies on the structure of capsaicin beginning with its isolation in 1876 (40). After early controversary, capsaicin was found to be a mixture of similar compounds. The term "capsaicinoids" is now used to indicate capsaicin and its analogs. The term "capsaicin" is reserved for the major component among the capsaicinoids, N(-4hydroxy-3-methoxybenzyl)-8-methylnon-6-transenamide. Of special importance, the analogs do not produce equivalent oral burns. This is one of the reasons for variation in the burn produced by the many varieties of chili pepper.

Source of the burn. When capsaicin is applied to skin or mucous membrane it produces a burning pain. Jancsó and Szolcsanyi's pioneering studies (e.g., (41, 42)) ultimately led to the conclusion that capsaicin excites polymodal nociceptors (sensitive to noxious heat, mechanical and chemical stimulation) as well as warm thermoreceptors. Capsaicin stimulates by directly opening certain ion channels in membranes. Although not all pain is mediated via the polymodal nociceptors that capsaicin stimulates, these nociceptors are the most abundant (45). To distinguish between pain associated with capsaicin and the pain due to oral pathology, the pain produced by capsaicin will be referred to as "burn."

Capsaicin Desensitization of Pain Receptors.

Repeated applications of capsaicin produce less burning; this is called desensitization. The mechanism of capsaicin desensitization is not completely understood but appears to involve several processes one of which is the block of the voltage activated calcium channels that are opened by capsaicin stimulation (44). Because the neurons that capsaicin desensitizes are the most abundant pain neurons, desensitization of them is extremely clinically important. Local Application of Capsaicin for Pain Control. Topical capsaicin has been used for a variety of clinical conditions, many of which are not very responsive to conventional analgesics. Most conditions involve neuropathic pain or pain resulting from neuronal damage. Neuropathic pain is extremely difficult to treat and is generally not very responsive to narcotics or nonsteroidals. Medications that are used for this type of pain include the antidepressants, anticonvulsants, and local anesthetics.

Several studies support the medical efficacy of locally applied capsaicin in a cream vehicle in neuropathic pain syndromes. A large multi-center trial with 277 patients demonstrated that topically applied capsaicin (0.025% or 0.075%), used for up to eight weeks significantly reduced pain and improved quality of life in both post-herpetic neuralgia and diabetic neuropathy (46–51). Other neuropathic pain syndromes where capsaicin has been shown to be effective include postmastectomy pain (46, 52), stump pain (53), trigeminal neuralgia (54), reflex sympathetic dystrophy (55), and Guillain-Barre syndrome (56). Topical capsaicin has also been shown to decrease the pain associated with rheumatoid and osteoarthritis (57), and intra-nasal capsaicin spray has been shown to reduce the pain associated with cluster headaches (58).

Other uses for capsaicin where significant improvement has been demonstrated include pruritis secondary to hemodialysis (59), notalgia paraesthetica (60), and psoriasis (61). The study done on patients with psoriasis revealed that capsaicin applied topically reduced scaling and erythema (61). Capsaicin has also been instilled into the bladder to treat bladder hyperreflexia (62,63), and it has been used to treat vasomotor rhinitis (64). Topical capsaicin has been shown to improve the ra te of re-epitheliazation of wounds in a model of wound healing in mini-pigs (65), thus it may be efficacious in wound healing in humans.

Since the neurons that capsaicin desensitizes are the most abundant neurons, desensitization with capsaicin should virtually abolish pain. However, in a review of capsaicin studies, Craft and Porreca note that "complete pain relief was rarely achieved, despite the lengthy treatment regimens" (66). The work discussed below shows that oral capsaicin desensitization is rapid and virtually complete, possibly because the oral mucosa is thinner than skin and so provides a less effective barrier. However, the mode of application may also play a role. Hawk et al used the same capsaicin cream as that used in the studies discussed above to treat oral postherpetic neuralgia. The patient was instructed to apply 0.025o capsaicin cream four times per day, noted a decrease in pain after two days, and total abolition of the pain four weeks later (67). This slow response was similar to that seen when capsaicin cream is applied to other loci on the skin.

Oral Capsaicin Burn

Methods of Assessing Oral Burn Sensations. There are some chili peppers that are hotter than others. The degree of heat of a pepper depends on the type of pepper. Since chili peppers are consumed themselves and are also used to produce seasonings (e.g., cayenne pepper, Tabasco sauce), there is considerable interest in the proper ties of capsaicin in the mouth on the part of consumers and those involved in the commercial preparation of chili pepper products. The need to quantify the intensity of the oral burning produced by capsaicin in a variety of products led to the development of new sensory methods.

In 1912, Scoville proposed a unit of oral burn that now bears his name, Scoville heat units (SHUs) (68). The method consists of diluting the sample of interest until it produces a just perceptible burn on the tongue. For example, if the sample were just barely perceptible, it's burn would be 1 SHU. If the sample had to be diluted to 1 part in 1000 parts to produce a just perceptible bum, then the burn of the original sample would be 1000 Scoville heat units. In these terms, pure capsaicin is considered to fall between 15 and 17 million SHUs (40). A jalapeno pepper measures between 2,500 and 5,000 SHUs while the habanero pepper, said to be the hottest in the world, measures between 200,000 and 300,000 SHUs (69).

In practice, the Scoville method is cumbersome and unreliable so sensory experts have sought substitute methods. Gillette and her co-workers developed a new method in 1984 (70) that utilizes a concentration series of pure capsaicin as standards. The oral burn produced by dilutions of chili pepper samples are then compared to this standard series.

In psychophysical studies of capsaicin in the mouth, the oral burn of pure capsaicin solutions of various concentrations has been assessed using the method of magnitude estimation (e.g., (71–75)). This method has the advantage of providing data with ratio properties. That is, subjects assign numbers to intensities such that if one stimulus burns twice as much as another, they rate it with a number twice as large. These studies have provided important information about the properties of capsaicin stimulation and desensitization in the mouth that is discussed in the next section.

Genetic and sex differences in the perception of oral burn. There is genetic variation in the ability to perceive the oral burn of chili peppers. This genetic variation is associated with the ability to taste, possibly because of the innervation of taste buds on the anterior or mobile portion of the tongue. In this area, taste buds are innervated by two nerves, the chorda tympani branch of the facial nerve (VII) which mediates taste and the trigeminal nerve (V) which mediates touch temperature, and pain (76, 77). The evidence for the association is as follows.

In 1931, Fox discovered that the compound phenylthiocarbamide (PTC) tasted bitter to some individuals but was tasteless to others (78). Subsequent family studies supported the conclusion that tasting is produced by a dominant allele, T. Nontasters carry two recessive alleles, tt, while tasters carry either one dominant allele, Tt, or two dominant alleles, TT (e.g., (79)). More recently, Bartoshuk and her colleagues have shown that some tasters find PTC/PROP (PROP is a chemical relative of PTC's that has supplanted PTC in taste studies) to be only moderately bitter while others find it to be intensely bitter. This suggests that PTC/PROP tasting may be incompletely dominant with three phenotypical groups: nontasters, medium tasters, and supertasters (80–83).

Taste buds can be counted on the tongues of living human subjects by videotaping the tongue surface through a microscope (84, 85). The densities of taste buds show dramatic differences with PROP taster status. In a recent study, nontasters (N=10) had an average of 120_+23 taste buds/cm2, medium tasters (N=23) had 350_+34 taste buds/cm2, and supertasters had 668+103 taste buds/cm2 at the tip of the tongue (86). In another study, a series of capsaicin solutions were applied to the anterior tongues of nontasters, medium tastes and supertasers (87). Supertasters perceived greater burn than medium or nontasters.

To test the idea that the enhanced burn supertasters experience is due to the trigeminal innervation supplied with the taste buds, capsaicin was applied to the anterior tongue (innervated by VII and V) and the floor of the mouth (innervated by V) in nontasters, medium tasters, and supertasters (87). Supertasters perceived greater burn on the anterior tongue but not on the floor of the mouth. This supports the idea that at least some of the trigeminal innervation of taste buds mediates oral burn.

Females are more likely than males to have large numbers of taste buds and to be PROP supertasters (86). This means that on the average, females perceive greater oral burn than males from capsaicin and may experience greater oral pain from pathology as well.

Other irritants do not desensitize pain receptors. Desensitization to capsaicin reduces burn sensations from a variety of other irritants (e.g., ethanol, and the irritant compounds in ginger, black pepper, and cinnamon) but other irritants do not desensitize capsaicin (e.g., (88–90)). The piperine in black pepper is one exception; however, even though repeated application of piperine does desensitize capsaicin to some degree, capsaicin desensitizes piperine much more effectively ((72)).

Oral Capsaicin Desensitization

Temporal properties of desensitization. Green demonstrated that desensitization requires both the application and the removal of capsaicin (71, 91). For example, in one session of an experiment, Green applied capsaicin to the tongue for 10 minutes and then waited. At the end of 10 minutes the capsaicin was reapplied and produced essentially no burn. In a separate session he applied capsaicin in the same way for 10 minutes but instead of stopping, continued to apply capsaicin throughout the next 10 minutes. At that point, the capsaicin burned even more intensely than it had when initially applied. One could argue that capsaicin was removed from the pain receptors during the 10 minute wait in the first session and that this removal was critical to the desensitization.

However, Green noted that one might also argue that desensitization cannot occur when the pain neurons are activated whether or not capsaicin is present. Zingerone (derived from ginger) activates pain neurons but does not desensitize them. Green reasoned that if activation of the pain neurons prevented desensitization, then 10 minutes of capsaicin followed by 10 minutes of zingerone would fail to produce desensitization. This did not occur. After capsaicin and zingerone, a reapplication of capsaicin produced no burn. Thus Green conclusively demonstrated that desensitization to capsaicin requires both the application of the capsaicin and then its removal. This becomes very important in the clinical usage of capsaicin to produce successive desensitization (explained below).

Desensitization to a low concentration of capsaicin reduces the perceived burn of hi-her concentrations. Karrer and Bartoshuk (74, 75) desensitized the anterior portion of the tongue to either 10 ppm or 100 ppm and tested with a concentration series: 1, 10, 100, and 1000 ppm (see FIG. 3). These concentrations fall within the range found in various chili peppers and products made from them as shown in FIG. 1.

After one application, the effects of desensitization were complete at the desensitization concentration but also extended well above it. Desensitization to 100 ppm rendered 100 ppm virtually burn-free but also reduced the perceived burn of 1000 ppm more than 50%. Desensitization to 10 ppm reduced 100 ppm by about 50% and even reduced 1000 ppm by about 40%. This is an extremely important property of capsaicin for clinical applications. It suggests that a capsaicin concentration producing only a modest burn itself may be able to substantially reduce oral pain of much greater intensity.

Capsaicin applied to non-mucosal skin (e.g., arm) does not produce desensitization this rapidly. Patients must apply capsaicin cream several times per day to get maximal pain relief. In addition, the nearby skin becomes hypersensitive to warm stimuli during the desensitization process and this is why patients sometimes complain of pain from warm stimuli during the process. Capsaicin Desensitization as a Treatment for Oral Pain: complete with one application. FIG. 1 shows data collected from a patient with pain on the anterior tongue after radiotherapy (92). Capsaicin was applied for five minutes then the burn was allowed to fade. The patient's pain faded with it as shown in FIG. 2.

Capsaicin Desensitization of the Pain from Mucositis. Initial concern about exposing the lesions of mucositis to capsaicin was allayed by the experiment in mini-pigs in which capsaicin was associated with increased healing of skin wounds (65). Anecdotal reports from patients treated in oncology at Yale suggest that capsaicin may accelerate the healing of mucositis lesions. A vehicle found useful for delivery of capsaicin that was convenient, and acceptable to patients, and that would insure sufficient exposure to the capsaicin to produce desensitization is the subject of this invention. The applicants have developed a candy vehicle for the delivery of capsaicin. Candies containing 5–9 ppm capsaicin were made by adding cayenne pepper to a standard taffy recipe. The cayenne pepper, characterized chemically for its capsaicin content, was provided by Marianne Gillette, Director of the Sensory Evaluation Laboratory at the McCormick Spice company. The recipe follows.

1 cup sugar
¾ cup light corn syrup
⅔ cup water
1 Tbsp cornstarch
2 Tbsp butter or margarine
2 tsps vanilla
½ tsp. cayenne pepper Butter square pan, 8×8×2 inches. In 2-quart saucepan, combine sugar, corn syrup, water, cornstarch, butter and salt. Cook over medium heat, stirring constantly, to 256 on candy thermometer (or until small amount of mixture dropped into very cold water forms a hard ball). Remove from heat; stir in vanilla (or other flavoring) and cayenne pepper.

When just cool enough to handle, pull taffy until satiny, light in color and stiff. If taffy becomes sticky, butter hands lightly. Pull into long strips, ½ inch wide. With scissors, cut strips into 1-inch pieces. Wrap pieces individually in plastic wrap or waxed paper. (Candy must be wrapped to hold its shape). Makes about 1 pound.

The analgesic effects of this candy are shown in FIG. 3 for 10 patients for whom ECOG, Eastern Cooperative Oncology Group (4), assessments were available (see (93) for the first report from this ongoing study). Patients rated the pain produced by their mucositis verbally on a scale from 0 to 10, where 10 was the most intense pain ever experienced. Patients were instructed to allow the candy to dissove in the mouth without chewing it (this required approximately 10 minutes). After the candy had dissolved, the burn produced by the candy was allowed to fade (this required approximately 10 additional minutes). They were then asked to rate their pain once again. The reduction in pain was highly statistically significant (t=8.5, P<0.0001) as shown in FIG. 3. Successive Desensitization. Patients with a greater degree of pain will require a higher concentration of capsaicin to achieve optimal analgesia. The properties of capsaicin desensitization suggest a strategy by which patients can be desensitized to the concentration needed with minimal discomfort. First desensitize to a low concentration of capsaicin. After this is complete (note that the burn of the capsaicin must be allowed to fade to achieve complete desensitization), desensitize to a higher concentration. This higher concentration will produce less burn than normal because of the prior desensitization. After the second desensitization is complete, desensitize to yet a higher concentration, etc. FIG. 4 shows the results of a laboratory demonstration of successive desensitization (94). At each concentration, a large area completely incorporating the target area was desensitized. The next highest concentration was then tested on the target area. ANOVA and Tukey hsd tests (95) showed that both 10 and 100 ppm capsaicin were significantly reduced at the target area by successive desensitization as shown in FIG. 4.

Note that the capsaicin concentrations used in the successive desensitization study were quite high compared to the 5–9 ppm concentration in the cayenne pepper candies. This reflects spatial summation. The candies contact all of the oral mucosa. The capsaicin solutions were applied to a small area on the tip of the tongue. Capsaicin of 100 ppm applied to the entire oral mucosa would produce an extremely intense burn. Capsaicin is preferably employed in a range of 5–100 ppm.

Unfortunately, the concentration series of capsaicin that will produce optimal successive desensitization is not known, as yet. This concentrations for desensitization as well as the timing of the applications may vary with genetic status, sex, and the degree of mucositis. The effective amount of capsacin for effectivelly desensitizing a patient an be determined by known means and the effective amount of capsaicin level can be provided for in a confectionary composition.( or candy carrier).

An important aspect of the present invention includes a hard or soft confectionery composition incorporating an effective amount of capsaicin and a method for preparing the hard or soft confections containing the same. . In this form of the invention, the confectionery composition includes a pharmaceutically acceptable carrier such as a confectionery bulking agent, and an effective amount of capsaicin, and, optionally, various additives. The confectionery may be in the form of a lozenge, tablet, toffee, nougat, suspension, chewy candy, and the like. The pharmaceutically acceptable carriers may be prepared from a wide range of materials. Without being limited thereto, such materials include diluents, binders and adhesives, lubricants, disintegrants, coloring agents, bulking agents, flavoring agents, sweetening agents and miscellaneous materials such as buffers and adsorbents.

The preparation of confectionery formulations is historically well known and has changed little through the years. Confectionery items have been classified as either "hard" confectionery or "soft" confectionery. The capsaicin containing compositions of the present invention may be incorporated into confectionery compositions by admixing the capsaicin into conventional hard and/or soft confections.

As used herein, the term confectionery material means a product containing a bulking agent selected from a wide variety of materials such as sugar, corn syrup, and the like, and in the case of sugarless bulking agents, sugar alcohols such as sorbitol, mannitol, and the like, and mixtures thereof. Confectionery material may include such exemplary substances as lozenges, tablets, toffee, nougat, suspensions, chewy candy, chewing gum and the like. The bulking agent is present in a quantity sufficient to bring the total amount of confectionery composition to 100%.

Lozenges are flavored medicated dosage forms intended to be sucked and held in the mouth. Lozenges may be in the form of various shapes such as flat, circular, octagonal, and biconvex forms. The lozenge bases are generally in two forms: hard, boiled candy lozenges and compressed tablet lozenges.

Hard boiled candy lozenges may be processed and formulated by conventional means. In general, a hard boiled candy lozenge has a base composed of a mixture of sugar and other carbohydrate bulking agents kept in an amorphous or glassy condition. This amorphous or glassy form is considered a solid syrup of sugars generally having from about 0.5% to about 1.5% moisture. Such materials normally contain up to about 92% corn syrup, up to about 55% sugar and from about 0.1% to about 5% water, by weight of the final composition. The syrup component is generally prepared from corn syrups high in fructose, but may include other materials. Further ingredients such as flavoring agents, sweetening agents, acidulants, coloring agents, and the like may also be added.

Boiled candy lozenges may also be prepared from non-fermentable sugars such as sorbitol, mannitol, and hydrogenated corn syrup. Typical hydrogenated corn syrups are Lycasin, a commercially available product manufactured by Roquette Corporation, and Hystar, a commercially available product manufactured by Lonza, Inc. The candy lozenges may contain up to about 95% sorbitol, a mixture of sorbitol and mannitol in a ratio from about 9.5:0.5 up to about 7.5:2.5, and hydrogenated corn syrup up to about 55%, by weight of the solid syrup component.

Boiled candy lozenges may be routinely prepared by conventional methods such as those involving fire cookers, vacuum cookers, and scrapedsurface cookers also referred to as high speed atmospheric cookers. Fire cookers involve the traditional method of making a boiled candy lozenge base. In this method, the desired quantity of carbohydrate bulking agent is dissolved in water by heating the agent in a kettle until the bulking agent dissolves. Additional bulking agent may then be added and the cooking continued until a final temperature of 145° C. to 156° C. is achieved. The batch is then cooled and worked as a plastic-like mass to incorporate additives such as flavoring agents, coloring agents and the like.

A high-speed atmospheric cooker uses a heat-exchanger surface which involves spreading a film of candy on a heat exchange surface, the candy is heated to 165° C. to 170° C. in a few minutes. The candy is then rapidly cooled to 100° C. to 120° C. and worked as a plastic-like mass enabling incorporation of the additives, such as flavor agents, coloring agents, and the like. In vacuum cookers, the carbohydrate bulking agent is boiled at a temperature from about 125° C. to about 132° C., vacuum is applied and additional water is boiled off without extra heating. When cooking is complete, the mass is a semi-solid and has a plastic-like consistency. At this point, flavoring agents, coloring agents, and other additives are admixed in the mass by routine mechanical mixing operations.

The optimum mixing required to uniformly mix the flavoring agents, coloring agents, and other additives during conventional manufacturing of boiled candy lozenges is determined by the time needed to obtain a uniform distribution of the materials. Normally, mixing times of from about 4 to about 10 minutes have been found to be acceptable.

Once the boiled candy lozenge has been properly tempered, it may be cut into workable portions or formed into desired shapes. A variety of forming techniques may be utilized depending upon the shape and size of the final product desired. A general discussion of the composition and preparation of hard confections may be found in H. A. Lieberman, Pharmaceutical Dosage Forms: Tablets, Volume 1 (1980), Marcel Dekker, Inc., New York, N.Y. at pages 339 to 469, which disclosure is incorporated herein by reference.

The apparatus useful in accordance with the present invention comprises cooking and mixing apparatus well known in the confectionery manufacturing arts, and therefore the selection of the specific apparatus will be apparent to the artisan.

In contrast, compressed tablet confections contain particulate materials and are formed into structures under pressure. These confections generally contain sugars in amounts up to about 95%, by weight of the composition, and typical tablet excipients such as binders and lubricants as well as flavoring agents, coloring agents, and the like.

n addition to hard confectionery materials, the lozenges of the present invention may be made of soft confectionery materials such as those contained in nougat. The preparation of soft confections, such as nougat, involves conventional methods, such as the combination of two primary components, namely (1) a high boiling syrup such as a corn syrup, hydrogenated starch hydrolysate or the like, and (2) a relatively light textured frappe, generally prepared from egg albumin, gelatin, vegetable proteins, such as soy derived compounds, sugarless milk derived compounds such as milk proteins, and mixtures thereof. The frappe is generally relatively light, and may, for example, range in density from about 0.5 to about 0.7 grams/cc.

The high boiling syrup, or "bob syrup" of the soft confectionery is relatively viscous and has a higher density than the frappe component, and frequently contains a substantial amount of carbohydrate bulking agent such as a hydrogenated starch hydrolysate. Conventionally, the final nougat composition is prepared by the addition of the "bob syrup" to the frappe under agitation, to form the basic nougat mixture. Further ingredients such as flavoring agents, additional carbohydrate bulking agents, coloring agents, preservatives, medicaments, mixtures thereof and the like may be added thereafter also under agitation. A general discussion of the composition and preparation of nougat confections may be found in B. W. Minifie, Chocolate, Cocoa and Confectionery: Science and Technology, 2nd edition, AVI Publishing Co., Inc., Westport, Conn. (1980), at pages 424–425, which disclosure is incorporated herein by reference.

REFERENCES

1. Sonis, S. T., Oral complications of cancer therapy, in Cancer principles and practice of oncology, V. T. De Vita, S. Hellman, and S. A. Rosenberg, Editor. 1989, J. B. Lippincott: Philadelphia. p.2144–2152.
2. Sonis, S. T., Oral complications of cancer therapy, in Cancer: Principles and Practice of Oncology, V. T. De Vita, S. Hellman, and S. A. Rosenberg, Editor. 1993, J. B. Lippincott Co.: Philadelphia, Pa.
3. Peterson, D. E. and J. A. D'Ambrosio, Diagnosis and managment of acute and chronic oral complications of nonsurgical cancer therapies. Dental Clinics of North America, 1992. 36: p.945966.
4. Oken, M. M., R. H. Creech, D. C. Tormey, T. E. Davis, E. T. McFadden, and P. P. Carbone, Toxicity and response criteria of the eastern cooperative oncology group. American Journal of Clinical Oncology, 1982. 5: p. 649–655.
5. Conference, C., Oral complications of cancer–herapies: Diagnosis, prevention and treatment. Connecticut Medicine, 1989. 53: p. S9S–601.
6. Pfeiffer, P., E. L. Madsen, O. Hansen, and O. May, Effect of prophylactic sucralfate suspension on stomatitis induced by cancer chemotherapy. Acta Oncologica, 1990. 29: p. 171–173.
7. Shenep, J. L., D. Kalwihsky, P. R. Hudson, S. L. George, R. H. Dodge, K. R. Blankenship, and D. Thornton, Oral sucralfate in chemotherapy induced mucositis. Journal of Pediatrics, 1988. 113: p. 753–762.
8. Starasoler, S. and G. S. Haber, Use of vitamin E oil in primary herpes gingigostomatitis in an adult. New York State Dentistry, 1978. 44: p. 382.
9. Tampo, Y. and M. Yonaha, Vitamin E and glutathione are required for preservation of microsomal glutathione 5-transferase from oxidative stress in microsomes. Pharmacology, 1990. 66:p. 259–265.
10. Regan, V., E. Servinova, and L. Packer, Antioxident effects of ubiguinones in microsomes and mitrochondria are mediated by tocopherol recycling. Biochemical and Biophysical Research Communications, 1990. 169: p. 851–857.
11. Wadleigh, R., M. Redman, S. Cohen, and e. al, Vitamin E in the treatment of chemotherapy induced mucositis. Proc ASCO, 1990. 9: p. 320.
12. Wadleigh, R. G., R. S. Redman, M. L. Graham, and e. al, Vitamin E in the treatment of chemo-induced mucositis. American Journal of Medicine, 1992. 92: p. 481–484.
13. Mills, E. E., The modifying effect of beta-carotene on radiation and chemotherapy induced oral mucositis. British Journal of Cancer, 1988. 57: p. 416–417.
14. Schwartz, P. M., J. M. Dunigan, and J. C. Marsh, Allopurinol modification of the toxicity and antitumor activity of S-fluorouracil. Cancer Research, 1980. 40: p. 1885–1889.
15. Clark, P. I. and M. L. Selvin, Allopurinol mouthwash and 5-fluorouracil induced oral toxicity. European Journal of Surgical Oncology, 1985.11: p. 267–268.
16. Tsavaris, N., P. Caragiauris, and P. Kosmidis, Reduction of oral toxicity of 5-Fluorouracil by Allopurinol mouthwashes. European Journal of Surgical Oncology, 1988. 14: p. 405–406.
17. Loprinzi, C. L., S. G. Cianflone, A. M. Dose, P. Etzell, and e. al, A controlled evaluation of an Allopurinol mouthwash as prophylaxis against 5-Fu-induced stomatitis. Cancer, 1990. 65: p. 1879–1882.
18. Dose, A. M., D. Mahoud, and C. L. Loprinzi, A controlled trial of oral cryotherapy for preventing stomatitis in patients receiving 5-Fluoroural plus leucovorin: A North Central Cancer Treatment Group and Mayo Clinic Study. Proceedings of the American Society for Clinical Oncology, 1990. 9: p. 1242.
19. Mahoud, D. J., A. M. Dose, C. L. Loprinzi, and e. al, Inhibition of Fluorouracil-induced stomatitis by oral cryotherapy. Journal of Clinical Oncology, 1991. 9: p. 449–452.
20. Epstein, J. B. and P. Stevenson-Moore, Benzydamine hydrochloride in prevention and management of pain in oral mucositis associated with radiation therapy. Oral Surgery, Oral Medicine, and Oral Pathology, 1986. 62: p. 145–148.
21. Epstein, J. B., P. Stevenson-Moore, S. Jackson, and e. al, Prevention of oral mucositis in radiation therapy: A controlled study with benzydamine hydrochloride rinse. International Journal of Radiation Oncology, Biology, Physics, 1989.16: p. 1571–1575.
22. Lever, S. A., L. L. Dupuis, and S. L. Chan, Comparative evaluation of benzydamine oral rinse in children with antineoplastic-induced stomatitis. Drug Intelligence and Clinical Pharmacy, 1987.21:p.359–361.
23. Samaronayatie, L. P., A. G. Robertson, T. W. MacFarlane, I. P. Hunter, and e. al, The effect of chlorhexidine and benzydamine mouthwashes on mucositis induced by therapeutic radiation. Clinical Radiology, 1988. 39: p. 291–294.
24. Foote, R. L., C. L. Loprinzi, A. R. Frank, J. R. O'Fallon, S. Gulavita, H. H. Tewfik, M. A. Ryan, J. M. Earle, and P. Novotny, Randomized trial of a chlorhexidine mouthwash for alleviation of radiation-induced mucositis. Journal of Clinical Oncology, 1994.12: p. 2630–2633.
25. Matejka, M., A. Nell, G. Kiment, A. Schein, and e. al, Local benefit of prostaglandin E2 in radiochemotherapy-induced oral mucositis. British Journal of Oral and Maxillofacial Surgery, 1990. 28:p.89–91.
26. Porteder, H., E. Rausch, G. Kiment, G. Watzeti, and e. al, Local prostaglandid E2 in patients with oral malignancies undergoing chemo and radiotherapy. Journal of Cranio-MaxillaryFacial Surgery, 1988.16: p. 371–374.
27. Pillsbury, H. C., W. P. Webster, and J. Rosenman, Prostaglandid inhibitor and radiotherapy in advanced head and neck cancer. Archives of Otolaryngology Head and Neck Surgery, 1986.112: p.552–553.
28. Leveque, F. G., J. B. Parzuchowski, G. C. Facinacc, and e. al, Clinical evaluation of MGI 209, an anesthetic, film forming agentfor relieffrom painful oral ulcers associated with chemotherapy. Journal of Clinical Oncology, 1992.10: p. 1963–1968.
29. Leveque, F. G., Results of an open-labelled sequential study of MGI 209 for control of pain associated with chemotherapy-induced oral mucosal ulcerations. Topics on Supportive Care in Oncology, 1993. No. 11: p. 6–8.
30. Maciejewski, B., A. Zajusz, Pilecki, and e. al, Acute mucositis in the stimulated oral mucosa of patients during radiotherapy for head and neck cancer. Radiotherapy and Oncology, 1991.22: p. 7–11.
31. Carl, W. and L. S. Enrich, Management of oral mucositis during local radiation and systemic chemotherapy: A study of 98 patients. Journal of Prosthetic Dentistry, 1991. 66: p. 361–369.
32. Spijkervet, F. K., H. K. van Saere, J. J. Van Saere, and e. al, Mucositis prevention by selective elimination of the oralflora in irradiated head and neck cancer patients. Journal of Oral Pathology, 1990.19: p. 486–489.
33. Gabrilove, J. L., A. Jakubowski, H. Scher, and e. al, Effect of granulocyte colonystimulating factor on neutropenia and associated morbidity due to chemo for TCC of the urothelium. New England Journal of Medicine, 1988. 318: p. 1414–1422.
34. Poland, J., Prevention and treatment of oral complications in the cancer patient. Oncology, 1991. 5.
35. Miaskowski, C., Management of mucositis during therapy. National Cancer Institute Monographs, 1990.9: p. 95–98.
36. Knight, N., Pain and its relief: An exhibition at the National Museum of American History. 1983, Washington, D.C.
37. Andrews, J., Peppers: The Domesticated Capsicums. 1984, Austin, Tex.: University of Texas Press. 170.
38. MacNeish, R. S., Ancient Mesoamerican civilization. Science, 1964.143: p. 531–537.
39. Sahagun, B. d., General History of the Things of New Spain. Vol. 10. 1961, Santa Fe, N.Mex.: The School of American Research and the University of Utah.
40. Suzuki, T. and K. Iwai, Constituents of red pepper species: Chemistry, biochemistry, pharmacology, andfood science of the pungent principle of capsicum species, in The Alkaloids. 1984, Academic Press: Orlando, Fla. p. 227–299.
41. Jancso, N., A. Jancso-Gabor, and J. Szolcsanyi, Direct evidencefor neurogenic inflammation and its prevention by denervation and by pretreatment with capsaicin. British Journal of Pharmacology and Chemotherapy, 1967. 31: p. 138–151.

42. Szolcsanyi, J., A phar-nacological approach to elucidation of the role of different nervefibres and receptor endings in mediation of pain. Journal of Physiology (Paris), 1977. 73: p. 251–259.
43. Bevan, S. and J. Szolcsanyi, Sensory neurone specific actions of capsaicin: Mechanism and applications. Trends in Pharmacological Sciences, 1990. 11: p. 330333.
44. Dray, A., Neuropharmacological mechanisms of capsaicin and related substances. Biochemical Pharmacology, 1992. 44: p. 611–615.
45. Dray, A., Mechanism of action of capsaicin-like molecules on sensory neurons. Life Sciences, 1992. 51: p. 1759–1765.
46. Watson C. P. N., R. J. Evans, V. R. Watt, and N. Birkett, Post-herpetic neuralgia: 208 cases. Pain, 1988. 35: p. 289–297.
47. Bernstein, J. E., D. R. Bickers, M. V. Dahl, and J. Y. Roshal, Treatment of chronic postherpetic neuralgia with topical capsaicin. Journal of the Americal Academy of Derrnatology, 1987. 17:p.93–96.
48. Bernstein, J. E., N. J. Korman, D. R. Bickers, M. V. Dahl, and L. E. Millikan, Topical capsaicin treatment of chronic postherpetic neuralgia. Journal of the American Academy of Dermatology, 1989. 21: p. 265–270.
49. Bucci, F. A., C. F. Gabriels, and G. B. Krohel, Successful treatment of postherpetic neuralgia with capsaicin. American Journal of Ophthalmology, 1988.106: p. 758–759.
50. Scheffler, N. M., P. L. Sheitel, and M. N. Lipton, Treatment of painful diabetic neuropathy with capsaicin 0.075%. Journal of the American Podiatric Medical Association, 1991.81: p. 288–293.
51. Group, C. S., Treatment of painful diabetic neuropathy with topical capsaicin: A multicenter, double-blind, vehicle-controlled study. Archives of Internal Medicine, 1991. 151: p. 2225–2229.
52. Watson, C. P. N., R. J. Evans, and V. R. Watt, The post-mastectomy pain syndrome and the effect of topical capsaicin. Pain, 1989. 38: p. 177–186.
53. Weintraub, M., A. Golik, and A. Rubio, Capsaicin for treatment of post-traumatic amputation stump pain. Lancet, 1990. 336: p. 1003–1004.
54. Fusco, B. M. and M. Alessandri, Analgesic effect of capsaicin in idiopathic trigeminal neuralgia. Anesthesia and Analgesia, 1992. 74: p. 375–377.
55. Cheshire, W. P. and C. R. Snyder, Treatment of reflex sympthetic dystrophy with topical capsaicin: Case report. Pain, 1990. 42: p. 307–311.
56. Morgenlander, J. C., B. J. Hurwitz, and E. W. Massey, Capsaicin for the treatment of pain in Guillan-Barre Syndrome. Annals of Neurology, 1990. 28: p. 199.
57. Deal, C. L., J. J. Schnitzer, E. Lipstein, J. R. Seibold, R. M. Stevens, M. D. Levy, D. Albert, and R. Renold, Treatment of arthritis with topical capsaicin: A double-blind trial. Clinical Therapeutics, 1991.13: p. 383–395.
58. Sicuteri, F., B. M. Fusco, S. Marabini, V. Campagnolo, C. A. Maggi, P. Geppetti, and M. Fanciullacci, Beneficial effect of capsaicin application to the nasal mucosa in cluster headache. Clinical Journal of Pain, 1989. 5: p. 49–53.
59. Breneman, D. L., J. S. Cardone, R. F. Blumsaek, R. M. Lather, E. A. Searle, and V. E. Polluch, Topical capsaicinfor treatment of hemodialysis related puritis. Journal of the American Academy of Dermatology, 1992. 26: p. 91–94.
60. Leibsohn, E., Treatment of notalgic paresthetica with capsaicin. Cutis, 1992. 49: p. 335–336.
61. Bernstein, J. E., L. C. Parish, M. Rappaport, M. M. Rosenbaum, and H. H. Roenigk, Effects of topically applied capsaicin on moderate and severe psoriasis vulgaris. Journal of the American Academy of Derrnatology, 1986.15: p. 504–507.
62. Maggi, C. A., G. Barbanti, P. Santicioli, P. Beneforti, D. Misuri, A. Meli, and D. Turnini, Cystometric evidence that capsaicin sensitive nerves modulate the afferent branch of micturition reflex in humans. Journal of Urology, 1989. 142: p. 1S0–544.
63. Fowler, C. J., D. Jewkes, W. I. McDonald, B. Lynn, and W. C. DeGroat, Intravesical capsaicinfor neurogenic bladder dysfunction. Lancet, 1992. 339: p. 1239. 64. Lacroix, J. S., J. M. Buvelot, B. S. Polla, and J. M. Lundberg, Improvement of symptoms of non-allergic chronic rhinitis by local treatment with capsaicin. Allergy, 1991. 21: p. 595–600.
65. Watcher, M. A. and R. G. Wheeland, The role of topical agents in the healing offullthickness wounds. Journal of Dermatologic Surgery and Oncology, 1989. 15: p. 1188–1195.
66. Craft, R. M. and F. Porreca, Treatment parameters of desensitization to capsaicin. Life Sciences, 1992. 51: p. 1767–1775.
67. Hawk, R. J. and L. E. Millikan, Treatment of oral postherpetic neuralgia with topical capsaicin. International Journal of Derrnatology, 1988. 27: p. 336.
68. Scoville, W. L., Note on capsicums. Journal of the American Pharmaceutical Association, 1912.1:p.453–454.
69. DeWitt, D. and N. Gerlach, The Whole Chile Pepper Book. 1990, Boston: Little, Brown, and Company.
70. Gillette, M. H., C. E. Appel, and M. C. Lego, A new method for sensory evaluation of red pepper heat. Journal of Food Science, 1984. 49: p. 1028–1033.
71. Green, B. G., Capsaicin sensitization and desensitization on the tongue produced by brief exposures to a low concentration. Neuroscience Letters, 1989.107: p. 173–178.
72. Green, B. G., Cross-sensitization and desensitization between capsaicin and piperine: Evidence of partial independence of sensory mechanisms. Chemical Senses, 1990. 15: p. 585–586.
73. Green, B. G., Temporal characteristics of capsaicin sensitization and desensitization on the tongue. Physiology and Behavior, 1991. 49: p. 501–505.
74. Karrer, T. and L. Bartoshuk, Capsaicin desensitization and recovery on the human tongue. Physiology and Behavior, 1991. 49: p. 757–764.
75. Karrer, T. and L. M. Bartoshuk, Effects of capsaicin desensitization on taste in humans. Physiology and Behavior, 1994. in press.
76. Whitehead, M. C., C. S. Beeman, and B. A. Kinsella, Distribution of taste and general sensory nerve endings in fungiform papillae of the hamster. Am. J. Anat., 1985.173: p. 185–201.
77. Silver, W. L. and T. E. Finger, The trigeminal system, in Smell and Taste in Health and Disease, T. V. Getchell, et al., Editor. 1991, Raven Press: New York. p. 97–108.
78. Fox, A. L., Six in ten "tasteblind" to bitter chemical. Science News Letter, 1931. 9: p.249.
79. Snyder, L. H., Studies in human inheritance. IX The inheritance of taste deficiency in man. Ohio Journal of Science, 1932. 32: p. 436–440.
80. Bartoshuk, L. M., K. Fast, T. A. Karrer, S. Marino, R. A. Price, and D.A. Reed, PROP supertasters and the perception of sweetness and bitterness. Chemical Senses, 1992.17: p. 594.
81. Bartoshuk, L. M., E. Conner, T. Karrer, K. Kochenbach, M. Palceso, D. Snow, M. Pelchat, and S. Danowski, PROP supertasters and the perception of ethyl alcohol. Chemical Senses, 1993. in press.
82. Bartoshuk, L. M., The biological basis of food perception and acceptance. Food Quality and Preference, 1993. 4: p. 21–32.
83. Bartoshuk, L. M., ed. Genetic and pathological taste variation: What can we learn from animal models and human disease? The Molecular Basis of Smell and Taste Transduction, ed. D. Chadwick, J. Marsh, andj. Goode. Vol. Ciba Foundaton Symposium179. 1993. John Wiley and Sons: New York. 251–267.
84. Miller, I. J. and F. E. Reedy, Variations in human taste bud density and taste intensity perception. Physiology and Behavior, 1990. 47: p. 1213–1219.
85. Reedy, F. E., L. M. Bartoshuk, I. J. Miller, V. B. Duffy, L. Lucchina, and K. Yanagisawa, Relationships among papillae, taste pores, and 6-n-propylthiouracil (PROP) suprathreshold taste sensitivity. Chemical Senses, 1993.18: p. 618–619.
86. Bartoshuk, L. M., V. B. Duffy, and I. J. Miller, PTC/PROP tasting: Anatomy, psychophysics, and sex effects. Physiology and Behavior, 1994. 56: p. 1165–1171.
87. Karrer, T., L. M. Bartoshuk, E. Conner, S. Fehrenbaker, D. Grubin, and D. Snow, PROP status and its relationship to the perceived burn intensity of capsaicin at different tongue loci. Chemical Senses, 1992.17: p. 649.
88. Szolcsanyi, J., Capsaicin type pungent agents producing pyrexia, in Handbook of Experimental Pharmacology, M. S. Milton, Editor. 1982, SpringerVerlag: New York.
89. Green, B. G., Capsaicin cross-desensitization: psychophysical evidence of sensory complexity in oral chemical irritation. Chemical Senses, 1991.16: p. 529.
90. Green, B. G., The effects of temperature and concentration on the perceived intensity and quality of carbonation. Chemical Senses, 1992.17: p. 435–450.
91. Green, B. G., Evidence that removal of capsaicin accelerates desensitization on the tongue. Neuroscience Letters, 1993. 150: p. 44–48.
92. Karrer, T. and L. M. Bartoshuk, Capsaicin desensitization can abolish oral pain. Chemical Senses, 1994. in press.
93. Berger, A., M. Henderson, W. Nadoolman, V. Duffy, D. Cooper, L. Saberski, and L. Bartoshuk, Oral capsaicin provides temporary relief for oral mucositis pain secondary to chemotherapy/radiation therapy. Journal of Pain and Symptom Management, 1995. in press.
94. Nadoolman, W., V. B. Duffy, A. M. Berger, and L. M. Bartoshuk, Successive desensitization: a low pain/high dose technique for oral capsaicin delivery. Chemical Senses, 1994. in press.
95. Keppel, G., Design and Analysis: A Researcher's Handbook. 3rd ed. 1991, Englewood Cliffs, N.J.: Prentice Hall.
96. Robbins, J., Care for a little hellish relish? Or try a hotsicle. Smithsonian, 1992. 22(10): p. 42–51.
97. Stevens, D. A. and H. T. Lawless, Putting out the fire: Effects of tastants on oral chemical irritation. Perception and Psychophysics, 1986. 39: p. 346–350.
98. Green, B. G., Sensory interactions between capsaicin and temperature in the oral cavity. Chemical Senses, 1986.11: p. 371–382.
99. Nasrawi, C. W. and R. M. Pangborn, Temporal effectiveness of mouth-rinsing on capsaicin mouth-burn. Physiology and Behavior, 1990. 47: p. 617–623.
100. Sleisenger, M. H. and J. S. Fordtran, ed. Gastrointestinal disease: pathophysiology, diagnosis, management. 1993, W. B. Saunders Company: Philadelphia, Pa.
101. Kelly, W. N., ed. Textbook of Internal Medicine. 1992, J. B. Lippincott Company: Philadelphia, Pa.
102. Kumar, N., J. C. Vij, S. K. Sarin, and B. S. Anand, Do chilis influence healing of duodenal ulcer? British Medical Journal, 1984. 288: p. 1803–1804.

What is claimed is:

1. A method for desensitizing oral tissue comprising the step of providing a candy composition to a mouth, where said candy comprises: 5 to 100 parts per million capsaicin; and a candy carrier.

* * * * *